United States Patent
Argy et al.

(10) Patent No.: US 6,689,814 B1
(45) Date of Patent: *Feb. 10, 2004

(54) USE OF DIALKYLDIALKYLAMMONIUM HALIDE FOR THE PREPARATION OF A VIRUCIDAL MEDICAMENT INTENDED TO BE ADMINISTERED BY THE SYSTEMIC ROUTE

(75) Inventors: Gilles Argy, La Queue les Yvelines (FR); Fernand Bricout, Paris (FR); André Cheymol, Dange Saint Romain (FR)

(73) Assignee: Hutchinson, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 83 days.

(21) Appl. No.: 09/200,977

(22) Filed: Nov. 30, 1998

(51) Int. Cl.$^7$ ................................................ A61K 31/14
(52) U.S. Cl. ...................................................... 514/642
(58) Field of Search ........................................ 514/642

(56) References Cited

U.S. PATENT DOCUMENTS 4,836,853 A * 6/1989 Gribi ............................ 106/35
4,902,720 A * 2/1990 Baldone ...................... 514/642

FOREIGN PATENT DOCUMENTS

| DE | 28 10 998 | | 9/1978 | | |
| FR | 2 743 982 | * | 1/1997 | .......... | A01N/35/04 |
| WO | WO 95/19766 | | 7/1995 | | |
| WO | WO 95/31966 | * | 11/1995 | ............ | A61K/9/06 |
| WO | WO 93/1650 | * | 1/1997 | .......... | A01N/25/08 |

OTHER PUBLICATIONS

Prince et al 112 CA: 164924m, 1990.*
Kawakatsu et al 111 CA:187580q, 1989.*
Siddiqul et al, 99CA:63829, Jan. 1983.*
Arando–Anzaldo et al., "Chemical Inactivation of Human Immunodeficiency Virus in Vitro" J. Virol. Methods, 1992, vol. 37, No. 1, pp. 71–81.
Kennedy et al., "Virucidal Efficacy of the Newer Quternary Ammonium Comounds" Journal of the American Animal Hospital Association, 1995, vol. 31, No. 3, pp. 254–258.
Kikuchi et al., "Bactericidal Activities of Four Disinfectants and Didecyldimethyl Ammonium Chloride against MRSA Strains Isolated in a Hospital" Bokin Bobai—Journal of Antibacterial and Antifungal Agents, 1996, vol. 24, No. 6, pp. 391–396.
Remington's Pharmaceutical Sciences, 14th Edition, Chapter 67, p. 1180.
Takasaki et al., "Bactericidal Action of a Quaternary Ammonium Disinfectant, Didecyldimethyl Ammonium Chloride, Against Staphilococcus Aureus" Japanese Journal of Toxicology and Environmental Health, 1994, vol. 40, No. 4, pp. 344–350.
Yamamoto et al., "Antimicrobial Activity of Various Cationic, Amphoretic Surfactants and These Mixtures" Bokin Bobai—Journal of Antibacterial and Antifiungal Agents, 1990, vol. 18, No. 10, pp. 477–483.

* cited by examiner

Primary Examiner—Russell Travers
(74) Attorney, Agent, or Firm—Morgan Lewis & Bockius LLP

(57) ABSTRACT

Methods of treating enveloped viruses with dialkyldialkylammonium halides are disclosed, along with associated pharmaceutical compositions.

9 Claims, 1 Drawing Sheet

Figure 1:
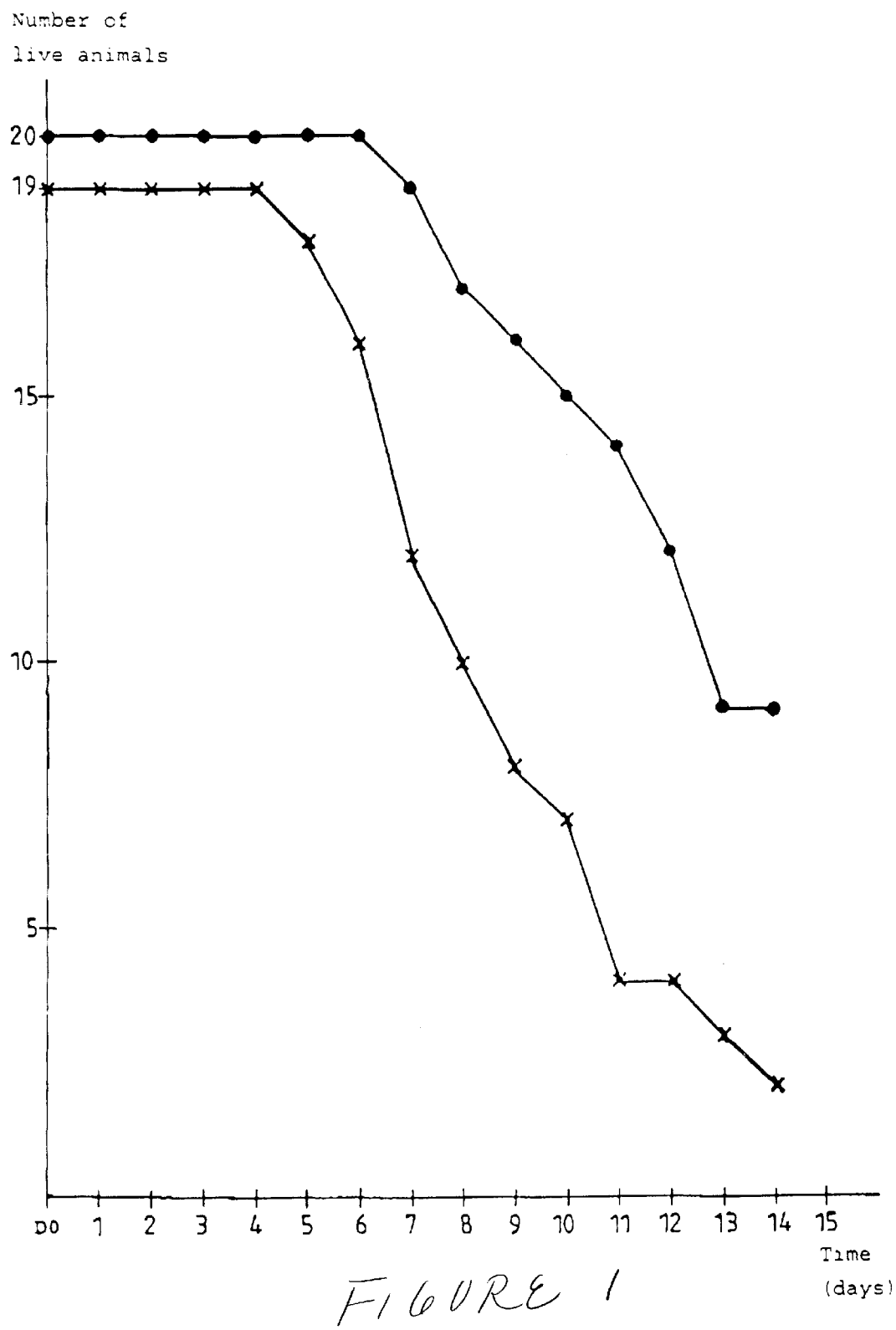

USE OF DIALKYLDIALKYLAMMONIUM HALIDE FOR THE PREPARATION OF A VIRUCIDAL MEDICAMENT INTENDED TO BE ADMINISTERED BY THE SYSTEMIC ROUTE

This Application claims Priority from French Patent Application No. 97/5075 filed Dec. 1, 1997.

FIELD OF THE INVENTION

The present invention relates to the use of a dialkyldialkylammonium halide having a virucidal effect, via the systemic route, in the prevention and treatment of enveloped virus infections, and in particular in the prevention of new viral outbreaks capable of occurring following an organ transplant.

BACKGROUND

The virucidal action of quaternary ammoniums, and in particular of a dialkyldialkylammonium halide, such as didecyldimethylammonium chloride (Bardac®) on enveloped viruses is known.

These compounds are indeed used via the external route to destroy the viruses present on work surfaces, on linen or for example on equipment.

Moreover, compositions containing a dialkyldialkylammonium halide have proved particularly effective as virucidal agents when they are included in gloves (European Application 0,555,116), in order to avoid possible accidental infection of surgeons or of paramedical staff via a needle or surgical knife contaminated with an enveloped virus, such as the human immunodeficiency virus (HIV), the hepatitis B and C viruses, or the herpes group of viruses.

Immunodepression, which is induced in patients who have had an organ transplant in order to limit the risks of graft rejection, makes the occurrence of an infectious episode extremely frequent in these patients following their operations. This may be either a reactivation of a virus already present in the transplant recipient but in a dormant state, or a first infection when the virus is introduced by the transplanted organ a seronegative patient. The most frequent viral infections are due to the Herpes simplex, Epstein-Barr and cytomegalovirus viruses, the latter alone having an incidence of more than 50%. The activity of hepatitis B and C is also increased after transplant.

It can therefore be understood that it is desirable to have antiviral agents capable of preventing new viral outbreaks in transplant recipients or of treating these new outbreaks so as to avoid diffusion of the virus into the whole body.

The antivirals currently proposed in the treatment of viral infections are generally virustatic and nonvirucidal: they do not destroy the virus itself, but they reduce the production of virus by the infected cell, that is to say that their target is a replicating viral population. This mechanism involves, inside the infected cells, the inhibition of one of the viral replication steps: attachment, penetration, decapsidation, transcription, assembly, maturation and release of the newly-formed viral particles (virions) out of the cell.

By way of example, this is the mode of action of aciclovir or 9-[(2-hydroxyethoxy)methyl]guanine, which acts on viral replication by inhibiting the DNA polymerase of herpesviruses. It is also mode of action of the antivirals described in U.S. Pat. No. 4,902,720 for example tetraethylammonium chloride, which acts on the assembly of the constituents of the virus during its replication inside the cells.

In spite of their importance, virustatic antivirals do not constitute a completely satisfactory solution to the problem of viral infections. Indeed, by virtue of their inhibitory action on viral replication, they induce the emergence of resistant mutants which may lead, in the long run, to a phenomenon of tachyphylaxis.

SUMMARY OF THE INVENTION

The applicant has therefore set itself the objective of providing a composition capable of having virucidal activity when it is administered by the systemic route, so as to avoid the appearance of viral resistance. In particular, the applicant has set itself the objective of providing a virucidal composition capable of effectively preventing new viral outbreaks in organ transplant recipients.

BRIEF DESCRIPTION OF THE DRAWING FIGURE

FIG. 1 compares the survival of a group of mice treated with Bardac® as compared with a control group.

The applicant has now found, unexpectedly, that compositions comprising, as active ingredient(s), one or more dialkydialkylammonium halides exhibit a virucidal action on enveloped viruses when they are administered by the systemic route, and this in a curative or preventive manner.

The subject of the present invention is therefore the use of a dialkydialkylammonium halide for the preparation of a virucidal medicament which is active on enveloped viruses and is intended to be administered by the systemic route, the alkyl groups of the dialkylammonium halide comprises from 1 to 14 carbon atoms.

"Systemic route" is understood to mean any general route of administration, namely the oral route (medicament being provided in the form of tablets, gelatin capsules, oral suspension and the like) or the parenteral route, such as administration by intramuscular, intravenous or subcutaneous injection, or any route other than the local external route.

Administration of said medicament is preferably carried out by the parenteral route.

According to a preferred embodiment of the use according to the invention, the daily dose of said dialkyldialkylammonium halide by the parenteral route is about 300 mg.

By way of example, said dialkyldialkylammonium halide is administered twice per day in an amount of 150 mg slow infusions), for 5 to 6 days.

Advantageously, said medicament is intended to be administered for a period of to 1 to 8 days.

According to an advantageous embodiment, said medicament is intended to be administered preventively.

In particular, said medicament is intended to be used in the prevention of new viral outbreaks post-organ transplant.

Said dialkyldialkylammonium halide preferably comprises from 1 to 10 carbon atoms.

Advantageously, said dialkyldialkylammonium halide is didecyldimethylammonium chloride (Bardac®).

Unexpectedly, the use according to the present invention is effective on all enveloped viruses, for example, and without limitation, HIV, the hepatitis B and C viruses and the herpesviruses (Herpes simplex, Epstein-Barr virus, cytomegalovirus and the like).

Under the abovementioned conditions, the dialkyldialkylammonium halide is not toxic for the body and exhibits a virucidal action, that is to say that it destroys the envelope of the virus present in the blood stream (extracellular, circulating virus). The use according to the present invention does not therefore act on the multiplication of the virus in the cells; this characteristic makes it possible to avoid the appearance of mutant viruses, the genome of the virus not being affected.

Since new viral outbreaks post-transplant are extremely frequent and often extremely serious, and since the date of their occurrence after transplant is often predictable, the preventive treatment of patients with a composition according to the invention is particularly advantageous and important.

In addition to the preceding features, the invention further comprises other features which will emerge from the description which follows, which refers to exemplary embodiments of the subject of the invention, as well as to the accompanying FIG. 1, which shows, in the form of curves, the number of live mice as a function of the number of days, in a group of mice which have been infected with a Herpes simplex virus and treated with a composition in accordance with the invention (-●-) and that obtained for a control group (-x-).

It should be clearly understood, however, that these examples are given solely by way of illustration of the subject of the invention and do not in any manner constitute a limitation thereto.

EXAMPLE 1 a) Materials

Three-week-old female nu/nu Nude mice, having an average weight of 6 to 8 g, divided into two batches of 20 animals, a control group receiving only the virus (curve -x- in FIG. 1), and one group being treated with Bardac® (curve -●- in FIG. 1).

Herpesvirus simplex batch having a titer of 10' PFU (Plaque Forming Units)/ml.

Didecyldimethylammonium chloride (Bardac®) provided by the Swiss company Lonza and used in the form of a dilution in an isotonic saline solution.

b) Methods

Inoculation of the virus: 30 µl by the nasal route of pure viral suspension, which corresponds to an installation of about $10^4$ PFU (viral load). The inoculation is carried out according to the protocol described by KERN et al. in *Antiviral Res.*, 1986, 6, 189–195. One mouse died during the nasal instillation.

Bardac®: inoculation by the intraperitoneal route, twice a day of a dose of 0.025 mg of the product by injection, i.e. a daily dose of 0.050 mg. According to the manufacturer (LONZA), the $LD_{50}$ by the intravenous route is about 0.20 mg/10 g of mouse.

On day D0, Bardac® is injected in the morning, and 4 hours later nasal instillation of the virus is carried out, followed 6 hours later by the second injection of Bardac®; on the following days, the injections were carried out around 9 am and 5 pm. Daily monitoring was conducted for fourteen days, the animals found dead or exhibiting neurological disorders, such as paralysis, being considered to be infected.

c) Results

FIG. 1, which comprises on the x-axis the number of days and on the y-axis the number of live animals, makes it possible to deduce the percentage of survivals: 10% in the control group and 45% in the treated group, with an average duration of the disease of 8.5 days for the control group and 9.2 days for the treated group; the latter two figures show a difference in duration which is quite similar to those observed by KERN et al. (ibid), who studied the action of aciclovir (direct action on replication because of its penetration into viral cells) on the same animal model.

EXAMPLE 2 a) Materials and methods

A test similar to the one described in Example 1 was carried out using two groups of 17 mice, one Herpesvirus simplex batch having a titer of $2\times10^2$ PFU/ml, by inoculating a Bardac® dose of 0.018 mg by injection (that is to say a daily-dose of 0.036 mg) and following the protocol below: on day D0, Bardac® is injected and, 12 hours later, nasal instillation of the virus is carried out, followed by intraperitoneal injections of Bardac® every twelve hours. Monitoring was carried out twice per day for six days.

At the end of the monitoring period, the lungs of the animals in the two groups were collected for culturing, in order to detect the presence of the virus. Detection of the virus is carried out as follows: the lung is homogenized in a DOUNCE® mixer and then suspended in a sterile test tube and centrifuged for 10 minutes at 2000 rpm. If the sample is not analyzed immediately, it is stored at −80° C. The infectious titer of the lung is given by titrating the virions present in 0.3 ml of centrifugation supernatant and multiplying the number of PFU by ten.

b) Results

In the control group, five mice are alive on day D6, that is to say a percentage of survivals of 29%. This percentage is 59% in the treated group (ten mice alive on day D6).

Among the total number of mice in each group, 88% of the mice are infected in the control group (15 infected mice), against 41% in the treated group (7 infected mice).

Table 1 represents the infectious titer values (in PFU) measured in the lungs of the 17 mice in each group.

TABLE 1

| Control mice | PFU | Treated mice | PFU |
| --- | --- | --- | --- |
| Dead at D2 | 600 | Dead at D5 | 0 |
| Dead at D2 | >1000 | Dead at D6 | 0 |
| Dead at D5 | 100 | Dead at D6 | 20 |
| Dead at D5 | 50 | Dead at D6 | 150 |
| Dead at D5 | 40 | Dead at D6 | 50 |
| Dead at D5 | 30 | Dead at D6 | 200 |
| Dead at D5 | 200 | Dead at D6 | 0 |
| Dead at D5 | >500 | Alive at D6 | 0 |
| Dead at D6 | 0 | Alive at D6 | 20 |
| Dead at D6 | 30 | Alive at D6 | 0 |
| Dead at D6 | 50 | Alive at D6 | 100 |
| Dead at D6 | 60 | Alive at D6 | 0 |
| Alive at D6 | >500 | Alive at D6 | 20 |
| Alive at D6 | 20 | Alive at D6 | 0 |
| Alive at D6 | 0 | Alive at D6 | 0 |
| Alive at D6 | 30 | Alive at D6 | 0 |
| Alive at D6 | 20 | Alive at D6 | 0 |
| Total | >3200 | Total | 560 |

It is apparent from these results that the group treated with Bardac® is less affected by the virus, both from the point of view of the mortality and the infectious titer measured.

EXAMPLE 3 a) Materials

The protocol followed is identical to that of Example 2 with two batches of 52 animals.

b) Results

On the sixth day, the number of live mice is 39 in the treated group and 22 in the control group, that is to say a percentage of survivors of 75% among the treated animals and 42% in the control group.

As for the number of mice infected with the virus, 13 were infected among the treated animals (that is to say 25%) and 37 in the control group that is to say 71%), thus confirming the results obtained in Example 2 and demonstrating the importance of the treatment with Bardac®.

Table 2 compares the infectious titer proportional to the number of virions found in the lungs of the infected mice, in each of the groups. Overall, the infectious titer (in PFU) is reduced by a factor of 3 in the animals treated with Bardac®.

TABLE 2

| Control mice (37 mice infected out of 52) | | Treated mice (13 mice infected out of 52) | |
|---|---|---|---|
| Dead at D3 | 500, >1000 | Dead at D3 | >1000, 50 |
| Dead at D4 | 250 | Dead at D5 | 300, 160 |
| Dead at D5 | 40, 180, 300, 850, >1000, >1000, 750, 400, 150, 500, 600, 500, 400 | Alive at D6 | 50, 40 120, 250, 80 >1000, 20 >1000, 20 |
| Dead at D6 | 20, 100, 20, 140, 20, 800, 30, 50, >1000, 200, 100 | | |
| Alive at D6 | 20, 100, 10, 150, 20, 100, 60, 250, 120, 200 | | |
| Total infectious titer (PFU) | >11930 | Total infectious titer (PFU) | >4100 |

The examples above demonstrates that the use of a dialkyldialkylammonium halide according to the invention makes it possible to limit the extent of the viral infection.

As is evident from the above, the invention is not at all limited to these embodiments, implementations and applications which have just been described more explicitly; on the contrary, it encompasses all the variants which may occur to the specialists in this field, without departing from the framework or the scope of the present invention.

What is claimed is:

1. A method for virucidally treating an enveloped virus infection in a patient, comprising systemically administering to the patient a didecyldimethylammonium halide at a virucidal dosage.

2. The method of claim 1, wherein the didecyldimethylammonium halide is administered by a parenteral route.

3. The method of claim 2, wherein the dose of the didecyldimethylammonium halide administered by the parenteral route is about 300 mg.

4. The method of claim 1, wherein the didecyldimethylammonium halide is administered for a period of 1 to 8 days.

5. The method of claim 1, wherein the didecyldimethylammonium halide is administered preventively.

6. The method of claim 5, wherein the didecyldimethylammonium halide is administered for the prevention of viral outbreaks following an organ transplant procedure.

7. The method of claim 1, wherein the alkyl groups of the didecyldimethylammonium halide each comprise from 1 to 10 carbon atoms.

8. The method of claim 1, wherein the didecyldimethylammonium halide is didecyldimethylammonium chloride.

9. The method of claim 1, wherein the enveloped virus is selected from the group consisting of HIV, Hepatitis B, Hepatitis C, and herpes viruses.

* * * * *